United States Patent [19]

MacMillan et al.

[11] 3,953,599

[45] Apr. 27, 1976

[54] COMPOSITIONS FOR TOPICAL APPLICATION TO ANIMAL TISSUE AND METHOD OF ENHANCING PENETRATION THEREOF

[75] Inventors: Francis S. Kilmer MacMillan; Warren I. Lyness, both of Cincinnati, Ohio

[73] Assignee: The Procter & Gamble Company, Cincinnati, Ohio

[22] Filed: Jan. 17, 1975

[21] Appl. No.: 541,901

Related U.S. Application Data

[60] Division of Ser. No. 489,649, July 18, 1974, Pat. No. 3,903,256, which is a division of Ser. No. 224,356, Feb. 7, 1972, Pat. No. 3,839,566, which is a division of Ser. No. 48,655, May 17, 1970, Pat. No. 3,678,156, which is a division of Ser. No. 595,427, Nov. 18, 1966, Pat. No. 3,527,864, which is a continuation-in-part of Ser. No. 344,195, Feb. 12, 1964, abandoned.

[52] U.S. Cl. .............................. 424/265; 424/65; 424/337
[51] Int. Cl.² .................................. A61K 7/32
[58] Field of Search .................... 424/65, 265, 337

[56] References Cited

UNITED STATES PATENTS

| | | |
|---|---|---|
| 3,312,709 | 4/1967 | Kilmer-MacMillan .............. 260/292 |
| 3,326,768 | 6/1967 | Kilmer-MacMillan .......... 424/265 X |
| 3,527,864 | 9/1970 | Kilmer-MacMillan et al.. 424/337 X |
| 3,678,156 | 7/1972 | Kilmer-MacMillan et al. ....... 424/68 |
| 3,839,566 | 10/1974 | Kilmer-MacMillan et al.. 424/337 X |
| 3,903,256 | 2/1975 | Kilmer-MacMillan et al. ....... 424/59 |

OTHER PUBLICATIONS

F. S. Kilmer–MacMillan et al., J. Invest. Dermat. 43(5):363–377, Nov. 1964, "The Antiperspirant Action of Topically Applied Anticholinergics."

*Primary Examiner*—Shep K. Rose
*Attorney, Agent, or Firm*—Jerry J. Yetter; Julius P. Filcik; Richard C. Witte

[57] ABSTRACT

Disclosed are compositions for topical application to skin comprising an anticholinergic scopolamine ester in certain ($C_8$–$C_{12}$) aliphatic sulfoxides which enhance the penetration of the anticholinergic scopolamine ester through skin.

3 Claims, No Drawings

COMPOSITIONS FOR TOPICAL APPLICATION TO ANIMAL TISSUE AND METHOD OF ENHANCING PENETRATION THEREOF

This application is a division of application Ser. No. 489,649, filed July 18, 1974 now U.S. Pat. No. 3,903,256, issued Feb. 9, 1975; which in turn is a division of application Ser. No. 224,356, filed Feb. 7, 1972 now U.S. Pat. No. 3,839,566, issued Oct. 1, 1974; which in turn is a division of application Ser. No. 48,655, filed May 17, 1970, now U.S. Pat. No. 3,678,156, issued July 18, 1972; which in turn is a division of application Ser. No. 595,437, filed Nov. 18, 1966, now U.S. Pat. No. 3,527,864, issued Sept. 8, 1970; which in turn is a continuation-in-part of application Ser. No. 344,195, filed Feb. 12, 1964, now abandoned.

This invention relates to compositions for topical application to animal (this term as used herein includes both humans and lower animals) tissue and a method for enhancing the penetration of various substances through such tissue. More particularly, it relates to improved compositions for topical application and a method for enhancing the penetration of pharmacologically active substances through keratinized epithelial tissue.

The epidermal barrier to percutaneous absorbtion, i.e., the stratum corneum, is a nearly impermeable heterogenous animal tissue of which keratin is a major component. This tissue is found in animal skin, tongue, gingiva, esophagus, and vagina.

A wide variety of pharmacologically active substances are desirably applied topically to keratinized epithelial tissue for essentially local effect. It is known that various surfaceactive compounds improve the activity of such substances, apparently by enhancing the penetration of same through skin. For example, British Pat. No. 940,279, published Oct. 30, 1963, discloses that the presence of a surfactant in antiperspirant compositions based on anticholinergic agents appears to increase antiperspirant activity by providing more efficient absorption of the active agents at the site of application. It has been found, however, that many surface-active compounds enhance the permeability by actually damaging the barrier tissue. Indeed, the degree of penetration enhancement appears in some cases to be proportional to the extent of tissue damage. In any event, only slight to moderate enhancement of penetration is effected with the surface-active agents heretofore employed for this purpose in the prior art.

Certain organic solvents also serve to enhance penetration of substances through the epidermal barrier. For example, dimethylsulfoxide (D.M.S.O.) and homologous low molecular weight sulfoxides, when used in solvent concentrations, e.g., 50% or more, will enhance penetration of various substances. However, such compounds are systemically distributed in a very short time and can cause undesirable symptoms.

The desirability of enhancing the localized effects of such pharmacologically active substances as anesthetics, antimicrobial and antibiotic substances without adverse effects on the skin and with minimal general systemic involvement is readily apparent.

It is, therefore, an object of this invention to provide improved compositions for topical application to keratinized epithelial tissue and a method for enhancing the penetration of pharmacologically active substances through such tissue.

It is a further object of this invention to provide a method of enhancing the penetration of pharmacologically active substances through keratinized epithelial tissue without damaging said tissue or causing adverse systemic effects.

These and other objects are attained through a composition for topical application to animal tissue comprising a safe and effective amount of a pharmacologically active substance and from about 0.1% to about 10% of an aliphatic sulfoxide of the formula RSOR' wherein R is an alkyl, substituted alkyl, alkenyl or hetero group containing from 8 to 12 carbon atoms and R' is a low molecular weight alkyl or hydroxy-substituted alkyl group, in a pharmaceutically acceptable carrier.

By the term "pharmacologically active substance" as used herein is meant any chemical element or compound suitable for topical administration which induces any desired local transitory effect on living structures contacted therewith (sometimes referred to hereinafter as "penetrant"). Such substances include for example, anticholinergics, antimicrobials, antibiotics, antihistamines, local anesthetics, steroids, sunscreens, elemental sulfur and various metal ions such as aluminum, iron and zinc.

The "enhanced penetration" effected through the use of sulfoxides in accordance with this invention can be observed by measuring the rate of diffusion of pharmacologically active substances through guinea pig skin.

The sulfoxides which serve to enhance penetration in the compositions of this invention as hereinbefore stated have the formula RSOR' wherein R is a straight chain or branched chain alkyl, alkenyl, substituted alkyl or hetero group containing from 8 to 12 carbon atoms and R' is a low molecular weight alkyl or hydroxy-substituted group such as methyl, ethyl, propyl, $\beta$-hydroxyethyl or hydroxy-isopropyl.

If R contains less than 8 carbon atoms, substantially higher concentrations than the 10% maximum concentration specified herein must be employed to enhance penetration. For example, hexyl methyl sulfoxide must be used at a concentration of about 30% or more to significantly enhance penetration. The lower homologues must be used at solvent concentrations, e.g., 50% or more to accomplish this purpose. At these concentrations these lower sulfoxides (below $C_8$) can produce undesired systemic effects.

If R contains more than 12 carbon atoms the sulfoxide will not be soluble enough to provide the desired degree of penetration enhancement.

Substituted alkyl groups referred to in the foregoing definition of R in the one case includes hydroxyalkyl, lower alkoxyalkyl (e.g. methoxy) and ketoalkyl for example. Hetero groups include oxaalkyl, thiaalkyl, and azaalkyl for example.

The preferred sulfoxides for the purposes of this invention are the dialkyl sulfoxides wherein R is an alkyl or hydroxy-substituted alkyl group containing from 8 to 12 carbon atoms and R' is methyl, ethyl or propyl. SO in the above general formula is a representation of the sulfoxide group which is alternately expressed as $S \rightarrow O$, $S = O$, or $S^+ - O^-$. Examples of R include octyl, nonyl, decyl, undecyl, dodecyl, 3-decenyl, 2-dodecenyl, 3-undecenyl, 3-octenyl, 2-ketooctyl, 2-ketodecyl, 2-ketoundecyl, 2-ketododecyl, 2-hydroxyoctyl, 2-hydroxydecyl, 2-hydroxyundecyl, 2-hydroxydodecyl, 3-hydroxyundecyl, 3-methoxyundecyl, 2-methoxydodecyl, 3,6-dioxadodecyl, 2-ethylhexyl, and branched chain nonyl and dodecyl resulting from polymerization of three and four moles of propylene respectively.

Especially preferred dialkyl sulfoxides for the purpose of this invention are octyl methyl sulfoxide, nonyl methyl sulfoxide, decyl methyl sulfoxide, undecyl methyl sulfoxide, dodecyl methyl sulfoxide, 2-hydroxydecyl methyl sulfoxide, 2-hydroxyundecyl methyl sulfoxide and 2-hydroxydodecyl methyl sulfoxide.

The sulfoxide compounds disclosed herein can be used singly or in combination for the purpose of this invention. These compounds are readily obtainable by well known methods. For example, most can be prepared by the conventional method of first preparing the corresponding thioether and the oxidizing to the sulfoxide. The methods of carrying out these steps have recently been reviewed by A. Schoberl and A. Wagner (Methoden Organischen Chemie (Houben-Weyl), 4th Ed., Georg Thieme Verlog, Stuttgart, Vol. IX, pp. 97–143, 211–218 (1955)]. Further methods for preparing sulfoxide compounds are disclosed in U.S. Pat. Nos. 3,288,858; 3,288,859; and 3,288,860, granted Nov. 29, 1966.

The concentration of sulfoxide employed herein can range from about 0.1% to about 10.0% by weight. If concentrations less than about 0.1% are used the degree of penetration enhancement attained, especially with the lower chain length sulfoxides (e.g. octyl methyl sulfoxide), is not appreciable. If concentrations greater than about 10.0% are employed, solubility problems may be encountered with the higher chain length sulfoxides (e.g. dodecyl isopropyl sulfoxide) and no substantial improvement is seen. Preferably, the concentration of sulfoxide will range from about 1% to 8% by weight of the total composition.

The activity of the sulfoxides of this invention in enhancing skin penetration was shown by measuring the diffusion of various substances through guinea pig skin.

The enhancement of tissue penetration effected by the sulfoxides is observed with a variety of pharmacologically active substances as can be seen by permeability constant determinations by measuring the degree of physiological response of a given concentration of active substance with and without a sulfoxide. Penetration of metal ions can also be determined by staining sections of guinea pig skin which has been treated with solutions of said ions, with and without sulfoxide and microscopically examining the treated tissue or by X-ray fluorescence to obtain a semiquantitative measure of the respective degrees of penetration.

Normally, the stratum corneum is almost completely impervious to metal ions. Some penetration may occur into the most superficial layers from a simple aqueous solution but never exceeds the first 3 layers. When sulfoxides are added to such solutions in accordance with this invention, substantial concentrations of metal ions can be detected throughout the entire stratum corneum. Tests for metal ion penetration were undertaken in the following manner:

Test solutions were applied under closed patches to either the backs of abdomens of wax-depilitated guinea pigs 6 to 9 days after depilitation. The patches were retained from 1–4 hours after which the animals were sacrificed and skin biopsies taken. In some instances the test solutions were swabbed on the back with cotton and dried in a stream of air. In order to determine the duration the metal was retained in the skin, animals were sacrificed over a 2 week period following either type of application. Zinc was detected by a dithizone method on fresh cryostat cut sections. Iron was visualized by Perl's Prussian blue method on neutral formalin-fixed tissues. Aluminum was visualized by the aluminon method. Semi-quantitative data on the amount of metal in the tissue were obtained by analyzing separated epidermal sheets by X-ray fluorescence.

Zinc acetate (50 mM) and ferric chloride (50 mM) were each dissolved in 0.1M decylmethyl sulfoxide and applied under a closed patch for 4 hours. The X-ray fluorescence data are given in Table 1 below. These astringent salts are effective antiperspirants in combination with the aforesaid sulfoxide in these compositions.

TABLE 1

| Day After Application | Retention of Metal Salts Zinc Concentration $\mu g/q$ Dry Epidermis | Iron Concentration $\mu g/q$ Epidermis |
|---|---|---|
| Control (no application) | 80 | 7C |
| 1 | 3200 | 2300 |
| 3 | 1400 | 500 |
| 7 | 430 | 100 |

Compositions in accordance with this invention can be formulated with a wide variety of dermatologically acceptable ingredients of bases and in a number of physical forms. For example, such compositions may be in liquid or cream form and may be either aqueous emulsions or dispersions. Desirably, the active ingredients are uniformly dispersed in a water dispersible, dermatologically acceptable vehicle. Such a vehicle is non-toxic and is compatible with animal tissue, and does not prevent absorption of the active ingredients by these tissues. Such vehicles are well known in the pharmaceutical and cosmetic fields and their choice is not critical to the efficacy of the pharmacologically active substance and the sulfoxide penetration enhancing agent as long as they are water miscible. Examples of water dispersible dermatologically acceptable vehicles are water; water-soluble alcohols (monohydric and polyhydric alcohols — particularly lower alcohols $C_1$–$C_8$— e.g. ethanol, propanol, glycerol, sorbitol, 2-methoxyethanol, diethyleneglycol, monomethyl or diethyl ether, ethylene glycol, hexyleneglycol, mannitol, propylene glycol); polyethylene glycols and methoxypolyoxyethylenes (carbowaxes having molecular weight ranging from 200 to 20.000); glyceryl monolaurate, monopalmitate or monostearate; polyoxyethylene glycerols; polyoxyethylene sorbitols; and glucose. When alcohols or thier derivatives are used, some water is preferably included since such materials are usually hydroscopic.

Although the vehicle is preferably water miscible as stated above, petroleum based ointments and the like can also be used. For example, such substances as mineral oil, petroleum jelly, stearoyl diacetin, lanolin, paraffin and beeswax. Although they may tend to slow absorption they can be used, especially if there is sufficient water-dispersible vehicle present to provide a medium for absorption by animal tissue Emulsification of such substances also provides a means for their use. Oil-in-water emulsions such as cold cream bases can also be used.

An example of a cold cream contains: 13% stearic acid, 2% glyceryl monostearate, 5% olive oil, 0.5% potassium hydroxide and 73.5% water.

Since the compositions of this invention are to be topically applied to animal tissue, they should be formulated so that they have a pH in aqueous solution of not less than about 3.5 nor more than about 10.0. Irritation can be encountered at pH's lower than about 3.5 and the stability of various ingredients can be adversely affected at pH's higher than about 10.0.

The usual buffering materials can be used to adjust the pH to the desired range. Examples of such buffers are: glycine, citric acid, disodium hydrogen phosphate, potassium hydrogen tartrate, potassium hydrogen pthalate, and sodium hydrogen succinate.

A preferred embodiment of this invention is an antiperspirant composition containing a sulfoxide and an antiperspirnt ingredient uniformly dispersed in a dermatologically acceptable vehicle as hereinbefore described. The antiperspirant ingredient of such compositions can be an astringent salt such as the aluminum and zirconium salts as disclosed in U.S. Pat. Nos. 2,814,585; 2,854,382; and 2,906,668. Such salts comprise in combination an aqueous solution of a zironium or hafnium salt of a strong monobasic mineral acid and a basic aluminum compound. However, the aluminum salts of strong acids, especially the chloride and sulfate, are also useful. Aluminum chlorhydrate, for example, can be used to advantage in the compositions of this invention.

It has been found that safe and extremely effective antiperspirant compositions based on various anticholinergic compounds can also be prepared. Numerous operable anticholinergic compounds are disclosed at length in British Pat. No. 940,279 and by MacMillan et al. in J. Invest. Derm. 43:363 (1964) both incorporated herein by reference). Preferred anticholinergics for the purpose of this invention are the scopolamine esters set forth in the aforesaid publication. Especially preferred anticholinergic compounds are the paraalkoxybenzoyl esters of scopolamine. These compounds and a method for preparing same are disclosed by MacMillian in copending U.S. patent No. application Ser. No. 379,023, filed June 29, 1964 now U.S. Pat. No. 3,312,709, issued Apr. 4, 1967.

The anticholinergic compounds of especial utility in the compositions of this invention include the free base and acid salt forms of a compound having the general formula:

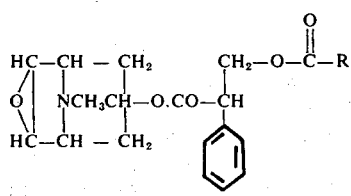

wherein:

is selected from the group consisting of a straight chain acyl group, a branched chain acyl group, an aromatic acyl group and acyclic acyl group, containing from 4 to about 12 carbon atoms.

Specific examples of the $C_4$–$C_{12}$ scopolamine esters that are especially useful as active antiperspirants according to this invention are:

trimethylacetyl scopolamine hydrochloride (pivaloyl scopolamine hydrochloride)
2-ethylbutyryl scopolamine hydrobromide
2-ethyl-3-methylbutyryl scopolmaine hydrobromide
n-butyryl scopolamine hydrobromide
n-valeryl-scopolamine hydrobromide
isovaleryl scopolamine hydrobromide
isopropylacetyl scopolamine hydrobromide
4-methylpentanoyl scopolamine hydrobromide
benzoyl scopolamine hydrobromide
2,4-dichlorobenzoyl scopolamine hydrobromide
cyclopentylpropionyl scopolamine hydrobromide
cyclohexylpropionyl scopolamine hydrobromide
naphthoyl scopolamine
n-hexanoyl scopolamine hydrobromide
n-heptanoyl scopolamine hydrobromide
n-octanoyl scopolamine hydrobromide
n-nonanoyl scopolamine hydrobromide
n-decanoyl scopolamine hydrobromide The above mentioned $C_4$–$C_{12}$ scopolamine esters can be prepared by any convenient well known method. Especially good preparative methods are described in U.S. Pat. No. 2,814,623.

Other less active anticholinergic compounds such as scopolammonium N-methyl bromide, trimethyl acetyl scopolamine methyl bromide, trimethylacetyl atropine hydrobromide, or benzoyl atropine hydrobromide can also be used to advantage in the present compositions due to the improved activity achieved by enhanced penetration.

If astringent salts are used as the antiperspirant agent in the compositions of this invention the concentration of this component should range from about 5% to about 50%. Preferably the concentrations of this pharmacologically active substance is from about 10% to about 30%. In general substantially greater antiperspirant effect is realized by a given concentration of astringent salt in compositions in accordance with this invention than is otherwise attainable.

If anticholinergic agents are used as the active ingredient in the antiperspirant embodiments, this component comprises from about 0.001% to about 0.25% by weight. Preferably, this pharmacologically active substance is used in concentrations ranging from 0.005% to 0.2%.

The method used to test the effectiveness of the antiperspirant compositions prepared according to this invention and other compositions with which they were compared is the "forearm" method, on human subjects.

The "forearm" test is primarily a qualitative test to determine whether a given composition has antiperspirant activity. However, with practice, grades can be readily given for visual results, as described below, to evaluate effectiveness. Grades are assigned from 0 (no antiperspirant effect) to 4 (complete perspiration inhibition), and 4+ (complete perspiration inhibition spreading beyond the treated area) with 3 being about 90% inhibition, 2 about 60% and 1 about 30%. In the "forearm" test, a given area of the forearm is treated three times with the composition to be tested over a period of 10 minutes, permitting the composition to dry each time. After 4 or 5 hours, the arm is washed and dried. A 1½% solution of iodine in ethanol is then painted over the area and allowed to dry. A slurry of starch and castor oil is then placed over the area and the subjects sits in a room at 100° F. for 5 to 15 minutes, depending on the subject. Any perspiration emitted permits iodine to react with the starch to give a visual indication (a blue-black color) of perspiration. To determine the length of effectiveness, the test can be repeated, with no re-application of the antiperspirant composition, after 48, 72, and 96 hours or more.

EXAMPLE I

The following compounds were compared using the forearm method. The anticholinergic compounds were in a 1% solution of the dialkyl sulfoxide at a concentration of 0.025 or 0.05% having a pH of approximately 4. The compounds were tested on the same eight male subjects, each, at the end of 5, 24, and 48 hours.

| Compound | Average Grade (8 subjects) | | |
|---|---|---|---|
| | 5 Hrs. | 24 Hrs. | 48 Hrs. |
| 0.05% scopolamine hydrobromide in water | 0.3 | 0.5 | 0.0 |
| 0.05% scopolamine hydrobromide in 1% 2-hydroxyundecyl methyl sulfoxide | 0.5 | 0.9 | 0.0 |
| 0.025% n-butyryl scopolamine hydrobromide in water | 2.5 | 2.4 | 1.1 |
| 0.025% n-butyryl scopolamine hydrobromide in 1% 2-hydroxyundecyl methyl sulfoxide | 3.5 | 4.0+ | 2.0 |

This comparison between representative scopolamine compounds with and without 2-hydroxyundecyl methyl sulfoxide establishes improved antiperspirant efficacy in the presence of the dialkyl sulfoxide. None of the compositions tested damaged the skin of the test subjects or caused systemic effects.

Antiperspirant embodiments of this invention are illustrated by the several formulations noted above as well as by the following example.

EXAMPLE II

Antiperspirant compositions having a pH of approximately 4 were formulated by combining the following ingredients.

| (A) | n-butyryl scopolamine hydrobromide | 0.025% |
|---|---|---|
| | 2-hydroxyundecyl methyl sulfoxide | 1.000% |
| | water | 98.975% |
| (B) | n-butyryl scopolamine hydrobromide | 0.025% |
| | water | 99.975% |
| (c) | n-butyryl scopolamine hydrobromide | 0.025% |
| | cetyl trimethylammonium bromide | 1.000% |
| | water | 98.975% |
| (D) | n-butyryl scopolamine hydrobromide | 0.025% |
| | sodium dodecylbenzene sulfonate | 1.000% |
| | water | 98.975% |

The preceding compositions were tested for antiperspirant efficacy by the previously described "forearm" method with the grading readings on eight subjects taken 24 hours after application.

Composition A was prepared according to the present invention. That is, it contained an anticholinergic scopolamine ester and as an enhancing agent, a dialkyl sulfoxide within the range previously described as being essential. This composition produced a 100% reduction in 24 hours, while Composition B containing only the anticholinergic scopolamine ester in an aqueous solution reduced perspiration by only 60%. Compositions C and D containing a cationic and anionic surfactant respectively resulted in no improvement whatsoever; specifically Composition C reduced sweating by 55% and Composition D was even less effective with a level of about 30% reduction in sweating.

Nonyl methyl sulfoxide, decyl methyl sulfoxide, undecyl methyl sulfoxide or dodecyl methyl sulfoxide can be used instead of the $\beta$-hydroxyundecyl methyl sulfoxide in Composition A with substantially equal results. Moreover, trimethylacetyl scopolamine hydrochloride and benzoyl scopolamine hydrobromide can be used in place of the n-butyryl scopolamine hydrobromide in the compositions presented in this example. No skin damage or systemic effects were observed in the test subjects.

An antiperspirant composition based on astringent salts is formulated as follows:

EXAMPLE III

| | Percent By Weight |
|---|---|
| Decyl methyl sulfoxide | 5.0 |
| Aluminum chlorhydrate | 7.5 |
| Zirconyl hydroxy chloride | 4.6 |
| Glycine | 2.0 |
| Glycerin | 3.0 |
| Titanium dioxide | 0.1 |
| Glycerol monostearate | 10.0 |
| Spermaceti | 2.0 |
| Butyl myristate | 4.0 |
| Behenic acid | 5.0 |
| Perfume | 0.2 |
| Dye, distilled water | Balance |
| pH | 4.5 |

When applied to human axillae, this composition substantially reduces the volume of perspiration and is more effective in this regard than a composition formulated as above but without decyl methyl sulfoxide. Moreover the enhanced penetration of the astringent salts is effected without damage to skin or systemic distribution of these salts.

A variety of compositions for topical application to animal tissue in accordance with this invention are set forth in the following examples.

EXAMPLE IV

A topical local anesthetic is formulated as follows:

|  | Percent By Weight |
| --- | --- |
| Procaine Hydrochloride | 6.0 |
| Nonyl methyl sulfoxide | 5.0 |
| Water | Balance |
| pH | Balance |
|  | 6.5 |

The above composition when applied to keratinized epithelial tissue produces a local anesthetic effect shortly after application. Nupercaine or pontocaine can be used in place of procaine in this composition, at a 2% concentration with similar effect.

The concentration of this pharmacologically active substance can be varied depending on the degree of anesthesia desired and the relative activity of the anesthetic chosen. Ordinarily this component will be used in a concentration of from 0.5% to 10%.

EXAMPLE V

A medicated face cream in accordance with this invention is formulated as follows:

|  | Percent By Weight |
| --- | --- |
| Decyl methyl sulfoxide | 4.5 |
| 3,5,4'-tribromosalicylanilide | 2.0 |
| Mineral Oil | 33.6 |
| Petrolatum | 25.0 |
| Stearyl Alcohol | 25.0 |
| Lanolin | 2.0 |
| Emulsifier | 5.0 |
| Ethylene Glycol | 1.5 |
| Distilled Water | 0.5 |
| TiO$_2$ | 0.7 |
| Perfume | 0.2 |

When applied to the face in accordance with ordinary practice, this composition provides greater control over acne and various infections of the skin than a similar formulation without sulfoxide.

The decyl methyl sulfoxide employed in this composition can be replaced with octyl hydroxy-isopropyl sulfoxide, nonyl ethyl sulfoxide, or dodecyl methyl sulfoxide with essentially equivalent results. Similarly the penetration of a wide variety of antibacterial agents is enhanced by the sulfoxides such that 3,5,4'-tribromosalicylanilide can be replaced by bis(3,5,6-trichloro-2-hydroxyphenyl)methane, bis(3,5-dichloro-2-hydroxyphenyl)sulfide, 3-trifluoromethyl-4,4'-dichlorocarbanilide, or mixtures thereof with good results. A number of antibacterial agents are described in U.S. Pat. No. 3,281,366, Judge et al.

Ordinarily the antibacterial component of compositions of this invention is employed at concentrations ranging from about 0.1% to 10%, preferably 1% to 5%.

EXAMPLE VI

A suntain oil in accordance with this invention is prepared as follows:

|  | Percent By Weight |
| --- | --- |
| Dodecyl methyl sulfoxide | 1.0 |
| 2-ethyl hexyl salicylate | 5.0 |
| Sesame Oil | 40.0 |
| Mineral Oil | 50.0 |
| Perfume, Color and antioxidant | Balance |

The efficacy of the sunscreen 2-ethyl hexyl salicylate is enhanced by virtue of the presence of the sulfoxide, as is seen when the efficacy of a similarly formulated product without sulfoxide is compared thereto.

Penetration of diverse sunscreens into the skin through conjoint application with sulfoxides in accordance with this invention can be demonstrated. Thus, 2-ethylhexyl salicylate employed in this example can be replaced by dipropyleneglycol salicylate, monoglyceryl p-aminobenzoate, digalloyl trioleate, menthylanthranilate and mixtures of these sunscreens with improved results.

EXAMPLE VII

An antibiotic mouthwash prepared in accordance with this invention is formulated as follows:

|  | Percent By Weight |
| --- | --- |
| Nonyl methyl sulfoxide | 0.2 |
| Gramicidin | .006 |
| Spearmint Oil | 0.05 |
| Menthol | .05 |
| Cinnamon Oil | .01 |
| Coloring | .001 |
| Saccharin sodium | 0.15 |
| Ethyl Alcohol | 25.0 |
| Water | Balance |

The efficacy of the antibiotic component in the treatment of local infection in the oral cavity is substantially improved by virtue of the sulfoxide content of said composition.

The penetration of other antibiotic substances through gingival tissue is also enhanced by sulfoxides. For example, penicillin, aureomycin, or tetracycline can be used in place of gramicidin in the above formulation to realize the benefits of this invention. This composition should be diluted with three to four parts of water before use.

EXAMPLE VIII

An antidandruff shampoo composition containing an antifungal agent in conjunction with a sulfoxide as essential components is formulated as follows:

|  | Percent By Weight |
| --- | --- |
| β-hydroxyundecyl methyl sulfoxide | 7.5 |
| Zinc 2-pyridinethiol-1-oxide | 2.0 |
| Sodium coconut alkyl glyceryl ether sulfonate (about 23% diglyceryl and the balance substantially monoglyceryl). | 25.0 |
| Sodium tallow alkyl glyceryl ether sulfonate (about 23% diglyceryl and the balance substantially monoglyceryl; the tallow alkyls correspond to those of substantially |  |

| | -continued<br>Percent By Weight |
|---|---|
| saturated tallow alcohols and contain approximately 2% $C_{14}$, 32% $C_{16}$, and 66% $C_{18}$). | 3.0 |
| Sodium chloride | 6.7 |
| Sodium sulfate | 3.3 |
| Sodium N-lauroyl sarcosinate | 3.8 |
| N-coconut acyl sarcosine | 1.2 |
| Diethanol amide of coconut fatty acids | 2.0 |
| Acetylated lanolin | 1.0 |
| Perfume | 0.4 |
| Color | 0.04 |
| Water | Balance |

This composition provides an effective means for treatment of dandruff when used in the conventional manner. The activity of other antidandruff agents can be improved by the presence of the sulfoxide in this formulation. Thus, selenium disulfide or sulfur can be used in place of zinc 2-pyridinethiol-1-oxide in this example.

EXAMPLE IX

A typical steroid-containing composition embodying this invention is formulated as follows:

| Hydrocortisone acetate | 9.0 | g. |
|---|---|---|
| Decyl methyl sulfoxide | 10.0 | g. |
| Methylparaben | 0.25 | g. |
| Propylparaben | 0.15 | g. |
| Propylene glycol | 120.0 | g. |
| Stearyl alcohol | 250.0 | g. |
| White petrolatum | 250.0 | g. |
| Distilled $H_2O$ | | |

When topically applied to keratinized epithelial tissue this ointment provides greater penetration of hydrocortisone acetate than can be achieved with the identical composition without the sulfoxide.

EXAMPLE X

A composition identical to that set forth in Example IX is prepared but replacing the hydrocortisone acetate with 20 g. of methapyrilene hydrochloride, a typical antihistamine. This composition is highly effective in treating allergic reactions.

The foregoing description of the invention has been presented describing certain operable and preferred embodiments. It is not intended that the invention should be so limited since variations and modifications thereof will be obvious to those skilled in the art, all of which are within the spirit and scope of this invention. Further, the range of concentrations of the pharmacologically active substances shown in the examples is not to be construed as the operable range since the effective amount of these substances will vary throughout a wide range and is contingent on the activity of the substance per se and the nature of the composition. In any case, the determination of amounts is within the skill of the ordinary physician. The amount employed will in all cases be the amount required to produce the desired response safely. The concentration ranges specified herein for various pharmacologically active substances reveal that is component can comprise as little as 0.001% by weight and as much as 50% by weight of the total composition. Percentages referred to in the foregoing specification and the following claims refer to weight percentages of the total composition unless otherwise specified.

It should be noted that the compositions and method of this invention find utility in veterinary medicine as well as in human applications.

What is claimed is:

1. A composition for application to animal tissue comprising a safe and effective amount of a anticholinergic scopolamine ester compound and from about 0.1% to about 10.0% of an aliphatic sulfoxide selected from the group consisting of octyl methyl sulfoxide, nonyl methyl sulfoxide, decyl methyl sulfoxide, undecyl methyl sulfoxide, dodecyl methyl sulfoxide, 2-hydroxydecyl methyl sulfoxide, 2-hydroxyundecyl methyl sulfoxide, and 2-hydroxydodecyl methyl sulfoxide.

2. The composition of claim 1 wherein the anticholinergic compound is selected from the group consisting of the free base and acid salt forms of a compound having the general structural formula:

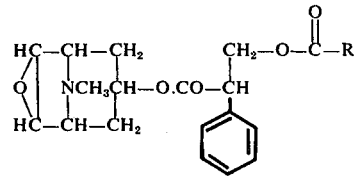

wherein

is selected from the group consisting of a straight chain acyl group, a branched acyl group, an aromatic acyl group and a cyclic acyl group, containing from 4 to about 12 carbon atoms.

3. The composition of claim 1 wherein the anticholinergic compound is para-methoxybenzoyl scopolamine.

* * * * *